United States Patent
Phillips

(10) Patent No.: US 11,232,411 B2
(45) Date of Patent: Jan. 25, 2022

(54) INTEGRATED HEALTHCARE SYSTEM

(71) Applicant: INNOVATION SPECIALISTS LLC, Houston, TX (US)

(72) Inventor: Clinton Glen Phillips, Houston, TX (US)

(73) Assignee: INNOVATION SPECIALISTS LLC, Houson, TX (US)

( * ) Notice: Subject to any disclaimer, the term of this patent is extended or adjusted under 35 U.S.C. 154(b) by 867 days.

(21) Appl. No.: 15/000,728

(22) Filed: Jan. 19, 2016

(65) Prior Publication Data

US 2016/0210433 A1    Jul. 21, 2016

Related U.S. Application Data

(60) Provisional application No. 62/104,616, filed on Jan. 16, 2015.

(51) Int. Cl.
*G06Q 10/10* (2012.01)
*G16H 40/67* (2018.01)
*G06Q 40/08* (2012.01)

(52) U.S. Cl.
CPC ......... *G06Q 10/1095* (2013.01); *G06Q 40/08* (2013.01); *G16H 40/67* (2018.01)

(58) Field of Classification Search
CPC ........ G06Q 40/08; G16H 10/60; G16H 50/20; G16H 10/20; G16H 15/00
See application file for complete search history.

(56) References Cited

U.S. PATENT DOCUMENTS

| | | | | |
|---|---|---|---|---|
| 2004/0017475 A1* | 1/2004 | Akers | ................... | G16H 10/60 348/207.1 |
| 2007/0226006 A1* | 9/2007 | Ruscio | ................... | G06Q 30/02 705/2 |
| 2009/0198509 A1* | 8/2009 | Dumoff | ................... | G06Q 30/02 705/2 |
| 2012/0166221 A1* | 6/2012 | Phillips | ................... | G06Q 10/00 705/3 |
| 2013/0110555 A1* | 5/2013 | Dunham | ................... | G06Q 40/08 705/4 |
| 2015/0278474 A1* | 10/2015 | Stueckemann | ........ | G06Q 10/10 705/2 |

* cited by examiner

*Primary Examiner* — Reginald R Reyes
(74) *Attorney, Agent, or Firm* — Polsinelli PC

(57) ABSTRACT

Disclosed is an integrated healthcare system. The integrated healthcare system including a server configured to receive and validate identification data, receive and verify coverage information associated with the identification data, and transmit, to a client, the validated identification data and the verified coverage information. The integrated healthcare system also including a client configured to receive, at a user interface, and transmit, to the server, the identification data. The client being further configured to receive, from the server, the validation of the identification data and display, on the user interface, one or more available benefits based on the validated identification data and the verified coverage information. The client being further configured to receive, at the user interface, an input command indicating selection of at least one of the one or more available benefits and initiate, a communication session based on the input command.

20 Claims, 6 Drawing Sheets

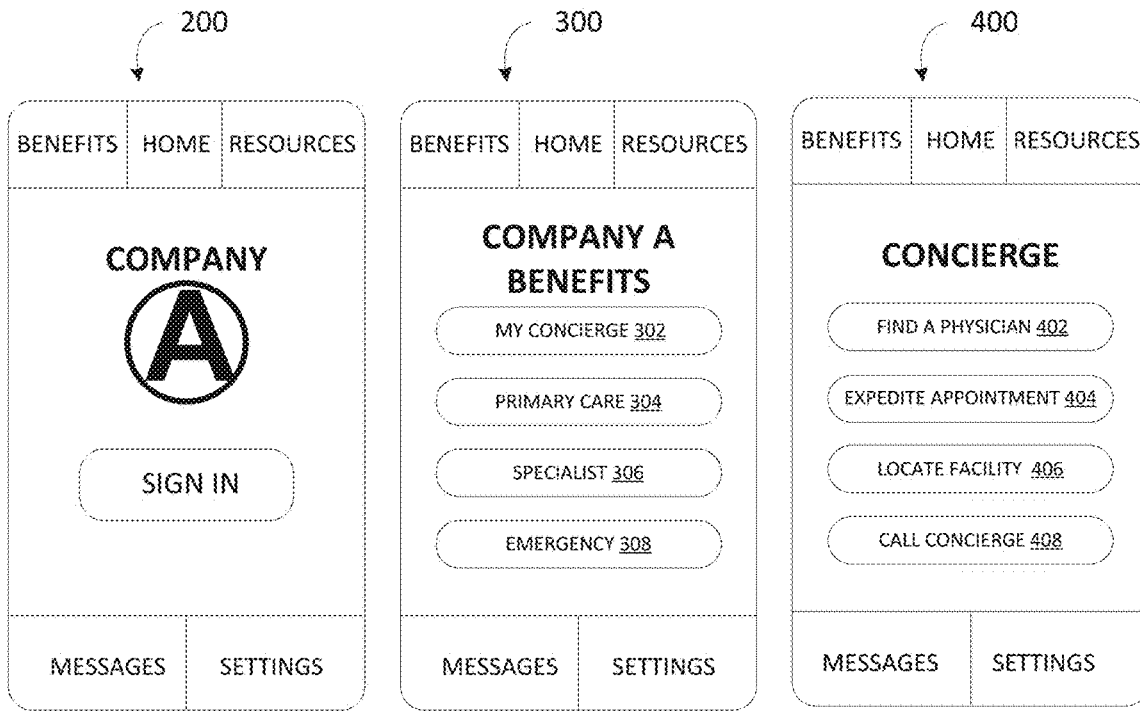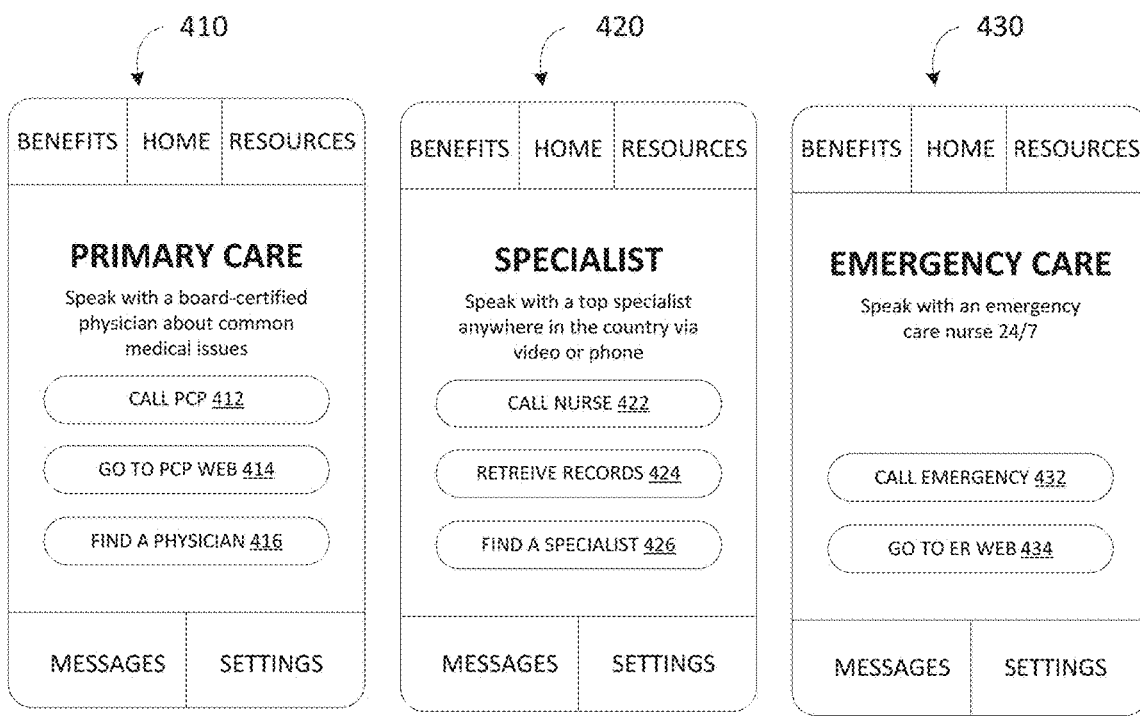

INTEGRATED HEALTHCARE SYSTEM

CROSS-REFERENCE TO RELATED APPLICATIONS

This application claims priority to U.S. provisional application Ser. No. 62/104,616 filed Jan. 16, 2015, which is hereby incorporated herein by reference in its entirety.

FIELD

The subject matter herein generally relates to an integrated healthcare system, and more specifically, improving the technical integration between multiple healthcare platforms.

BACKGROUND

Healthcare services often include multiple parties and online platforms (e.g., members, companies employing the member, insurance companies, physicians, hospitals, etc.). Members (i.e., patients) of the healthcare services may not know what type of services are available or needed. Providers (i.e., physicians, specialists, hospitals, clinics, etc.) may only provide certain healthcare services and accept certain insurances. Integrating the multiple parties and platforms can save time and efforts in locating, providing, and managing of healthcare services for the multiple parties and platforms.

BRIEF DESCRIPTION OF THE DRAWINGS

In order to describe the manner in which the features of the disclosure can be obtained, a more particular description of the principles briefly described above will be rendered by reference to specific examples thereof which are illustrated in the appended drawings. Understanding that these drawings depict only examples of the disclosure and are not therefore to be considered to be limiting of its scope, the principles herein are described and explained with additional specificity and detail through the use of the accompanying drawings in which:

FIG. 2-FIG. 9 illustrate client interfaces of an example integrated healthcare system;

DETAILED DESCRIPTION

Figure 1:
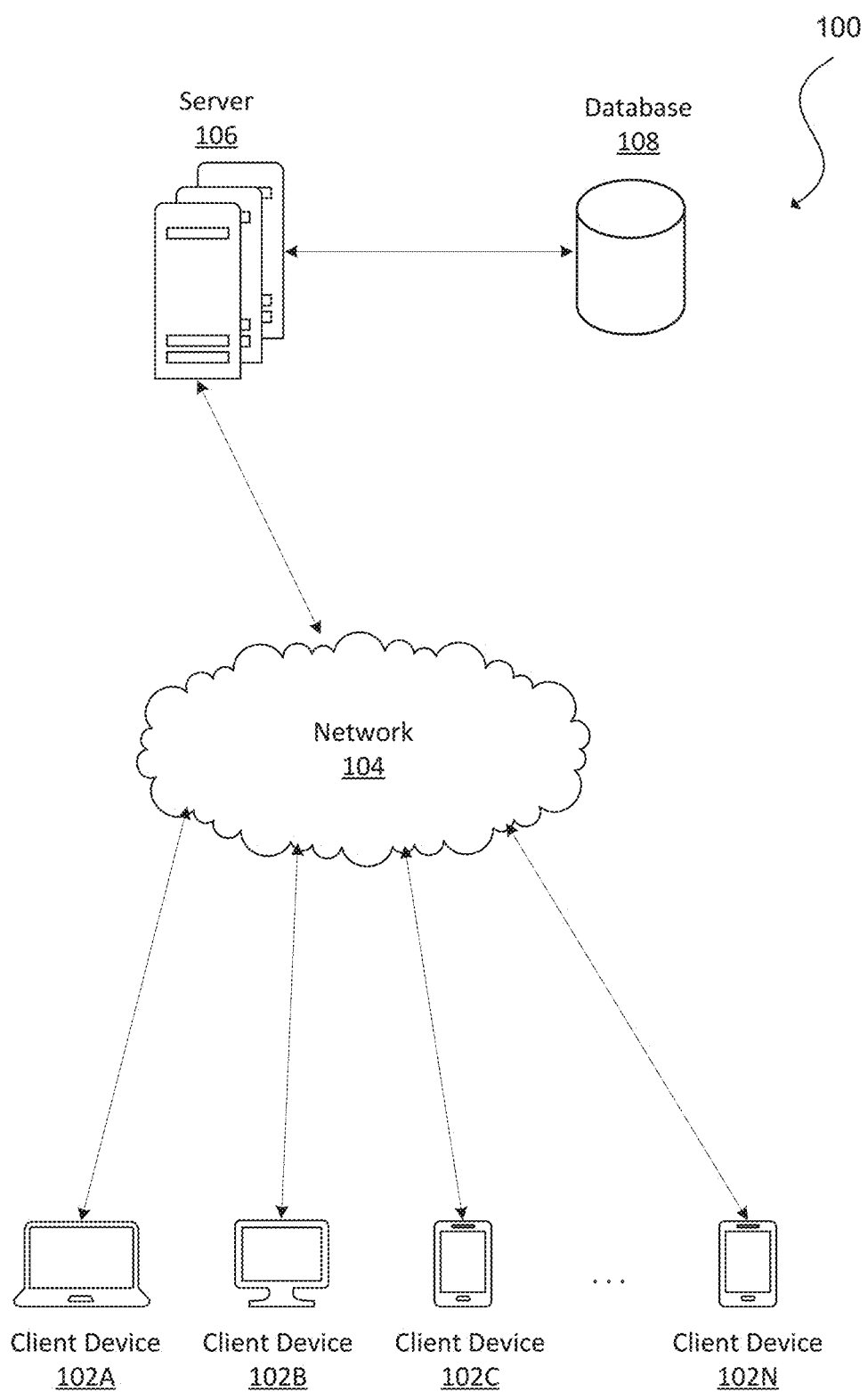
FIG. 1 is a block diagram of a system for an example integrated healthcare system.

Various examples of the disclosure are discussed in detail below. While specific implementations are discussed, it should be understood that this is done for illustration purposes only. A person skilled in the relevant art will recognize that other components and configurations may be used without parting from the scope of the disclosure.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Several definitions that apply throughout this disclosure will now be presented. The word "coupled" is defined as connected, whether directly or indirectly through intervening components, and is not necessarily limited to physical connections. The term "communicatively coupled" is defined as connected whether directly or indirectly through intervening components, is not necessarily limited to a physical connection, and allows for the transfer of data.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed is an integrated healthcare system. The integrated healthcare system can include a server configured to receive and validate identification data, receive and verify coverage information associated with the identification data, and transmit, to a client, the validated identification data and the verified coverage information. The integrated healthcare system can also include a client configured to receive, at a user interface, and transmit, to the server, the identification data. The client can be further configured to receive, from the server, the validation of the identification data and display, on the user interface, one or more available benefits based on the validated identification data and the verified coverage information. The client can be further configured to receive, at the user interface, an input command indicating selection of at least one of the one or more available benefits and initiate, a communication session based on the input command.

The integrated healthcare system can also be configured to transmit coverage information, receive verification of the coverage information, and populate the user interface with the coverage information, including a coverage card on the verified coverage information.

The communication session of the integrated healthcare system can at least be a telemedicine session, a voice communication with an emergency service, and/or conducted with a concierge (e.g., a human or automated system). The initiation of the communication session of the integrated healthcare system can include retrieving one or more records associated with the identification data, and/or scheduling an appointment.

With respect to implementing various examples of the disclosed technology, an example integrated healthcare system 100 is shown in FIG. 1, where electronic devices communicate by a network for the purposes of exchanging content and other data. The system can be configured for use on a wide area network (i.e., the Internet), as illustrated in FIG. 1. However, the present principles are applicable to a wide variety of network configurations that facilitate the intercommunication of electronic devices. For example, each of the components of system 100 of FIG. 1 can be implemented in a localized or distributed fashion in a network.

In integrated healthcare system 100, a user can interact with healthcare server 106 through client devices 102A, 102B, 102C, . . . , 102N (collectively "102") connected to network 104 by direct and/or indirect communication. Healthcare server 106 can include a single and/or multiple interconnected servers. Healthcare server 106 can support connections from a variety of different client devices 102, such as: desktop computers; mobile computers; mobile communications devices, e.g. mobile phones, smart phones, tablets; smart televisions; set-top boxes; and/or any other network enabled computing devices. Client devices 102 can be of varying type, capabilities, operating systems, etc. Furthermore, healthcare server 106 can concurrently accept connections from and interact with multiple client devices 102.

A user can connect to a healthcare server 106 through network 104 by a client interface installed on client device 102. For example, the client interface can be a stand-alone application, one or more application plug-ins, and/or a browser extension. However, the user can also interact with healthcare server 106 by a third-party application, such as a web browser, that resides on client device 102. In either example, the client interface can present a user interface (UI) for the user to interact with healthcare server 106. Client device 102 can receive input from the user and output information to the user through the client interface. For example, input can be letters, numbers, symbols, characters, or drawings. The input can be received through an input device (e.g., a camera, a touch screen, a mouse and/or keyboard, etc.) The output can be received at client device 102 through a network interface and displayed by the client interface.

Healthcare server 106 can enable a user (e.g., member, secondary member, etc.) to perform a variety of healthcare related tasks, such as, store profile data, retrieve and verify insurance coverage/benefits, locate healthcare services, calculate estimate costs, review insurance information including deductibles, as shown in FIG. 2-10. Healthcare server 106 can also enable verification of insurance coverage/benefits by connections to third-party services and employer benefit databases.

To facilitate the various healthcare services, a user can create an account (e.g., healthcare profile) with healthcare server 106. A healthcare profile can include personal information related to the user or the user's family. Personal information can include date of birth, age, nationality, weight, height, eye color, blood type, address, etc. The healthcare profile can also include current, past, and/or future insurance information/coverage/benefits of the user and members. For example, the insurance information/coverage/benefits can include deductibles, coinsurance, covered medical services/procedures, physicians, pharmacies, medicines, etc. The healthcare profile can also include the medical history of the user and the user's family. For example, appointments, medical procedures, telemedicine consultations, diagnoses, prescribed medicines, recommended treatments, past ailments, immunizations, bloodwork, etc. The healthcare profile can also receive and store health metrics through wearable electronic devices, non-wearable personal use medical devices, and/or user applications. For example, readings from wearable electronic devices can include smart watch, heart rate monitors, etc.; readings from non-wearable medical devices can include scales, glucose readers, oximeter, blood pressure reader, vitadock, etc.; and readings from user applications can include mapmyfitness, fatsecret, dailymile, strava, etc. The current health metrics can be blood pressure, blood sample results, weight, height, temperature, photographs, eye scans, heart rate, urine or fecal analysis results, fitness history, food intake history, oxygen intake, glucose readings, or any other user health metrics. In another example the user input can be via Human application programming interface (API). The current health metrics can be saved to a user's healthcare profile or transferred to a physician, specialist or nurse prior to or during a consultation. The healthcare service can also be restricted to a geographical area and/or costs.

Database 108 can be communicatively coupled to healthcare server 106 and can be configured to store the healthcare profiles; information regarding physicians/specialists (e.g., in-network and/or out-network, location, telemedicine availability, etc.); information regarding pharmacy locations; information regarding nurses (e.g., in-network and/or out-network, location, telemedicine availability, etc.), emergency services information, information regarding concierges (e.g., medical help or suggestions regarding the healthcare service), medicines, medical procedures, treatments, cost estimation for medical services; and information regarding hospitals (e.g., in-network and/or out-network, location, telemedicine availability, etc.).

The client interface installed on client device 102 can be configured to update and/or obtain the user profile data in database 108. Insurance companies and other third-parties can update and/or obtain data stored in database 108 by third-party applications running on electronic devices (e.g., client device 102, third-party servers, etc.). Database 108 can be one or more databases in a variety of configurations. For example, database 108 can be one or more relational databases. In other examples, database 108 can be a cloud-based storage or a content management system.

With respect to implementing various examples of the disclosed technology, example client interfaces are shown in FIG. 2-FIG. 10. Referring now to FIG. 2, a client interface illustrates an example sign-in interface 200. A user can sign-in (i.e., authenticate) to an integrated healthcare service. For example, a healthcare service can be provided by a company employing the user. In other instances, the healthcare service can be provided by independent companies, insurance providers, etc. By signing in, a healthcare profile for the user (and secondary users associated with the user) can be identified and provided after authentication. Authentication can include providing personal information (e.g., name, address, social security number, insurance information, etc.) and/or login credentials.

Referring now to FIG. 3, a client interface illustrates an example benefits screen 300 after a successful authentication (i.e., sign-in). Benefits screen 300 can present benefits provided by the healthcare service (e.g., by healthcare server 106). For example, benefits screen 300 can display available benefits to the user based on the healthcare profile of the user. In some examples, available benefits can be determined by insurance information/coverage/benefits and/or company benefits. In some examples, unavailable benefits can be a different color (e.g., grayed out) or be disabled (e.g., not selectable). Available benefits can include, but are not limited to, a concierge 302, a primary care physician 304, a specialist 306, and/or an emergency 308. The available benefits can be selectable by input from a user of client device 102. In some examples, input can be received from a touch screen/touch pads of client device 102. In other examples, the input can be through a mouse and/or keyboard. When an available benefit is selected, the client interface can present data corresponding to the selected benefit as shown in FIGS. 4A-4D.

Referring now to FIG. 4A, medical concierge benefit 400 can be presented on the client interface. Medical concierge benefit 400 can provide a plurality of concierge services, such as, find in-network physicians 402, schedule or expedite an appointment 404, locate a medical facility 406, and speak to concierge 408. The concierge services can be automated system or human interaction. In some examples, a human interaction can through a chat, voice call, video call, text message, email, or any method that enables a user the ability to ask questions and receive responses. The human interaction can be with a certified medical practitioner (e.g., a triage nurse, a registered nurse, nurse practitioner, physicians assistant, a physician, etc.). In other examples, the human interaction can be with a non-medical practitioner (e.g., an operator, insurance agent, etc.). In other examples, the concierge services can be provided by an automated system (e.g., automated voice system, automated interface, algorithmic system, selectable questions/answers, artificial intelligence, etc.). In other examples, in response to an input, information included in database 108 can be provided (e.g., physician list, physician profile, appointment calendar, location maps, etc.). In some examples, based on the user's input, a physician list can be generated. The physician list can include one or more in-network physicians, one or more out-of-network physicians, and/or a combination of in-network and out-of-network physicians. The physician list can also include medical facilities, specialists, locations, etc.

Referring now to FIG. 4B, primary care physician benefit 410 can be presented on the client interface. The primary care physician benefit 410 can provide access to a plurality of primary care physicians (PCP) through a telephone or video call 412, and/or a website 414. In other examples, a list of one or more PCPs 416 can be generated and presented on the client interface (e.g., using text, images, video, etc.). The list can be modified by user selectable filters (e.g., by conditions, questions, geographical location, price range, symptoms, illness, ratings from reviews, availability of telemedicine consultations, etc.). In some examples, the PCP list can include profiles of the PCP and/or links to the profiles. The PCP profiles can include information regarding education, length of practice, specialty, reviews from patients or peers, location, etc. The PCP profile can include information received from the PCP. The PCP profile can also include text, images, videos, or audio. In some examples, the PCP list can include practice names, hospitals, or any place that the PCP practices.

Referring now to FIG. 4C, specialist benefit 420 can be presented on the client interface. The specialist benefit 420 can provide access to a plurality of medical specialists (e.g., through a telemedicine session). In some examples, specialist benefit 420 can provide access to a specialist nurse 422. The specialist nurse can triage symptoms (e.g., by video call, voice call, etc.) to determine if a specialist consultation (e.g., telemedicine session) is appropriate and which type of specialist should be consulted. Specialist benefit 420 can also provide a retrieval of medical records 424 (e.g., stored in database 108). The records can be reviewed and transferred by the user to the specialist nurse and/or specialist. The records can also be downloaded or transferred to another user device (e.g., electronic mail, text message, short range wireless, etc.). In some examples, a list of one or more medical specialists 426 can be generated and presented on the client interface (e.g., using text, images, video, etc.). The list of medical specialists can be filtered in a similar manner to the PCP list, shown in FIG. 4B.

Referring now to FIG. 4D, emergency benefit 430 can be presented on the client interface. The emergency benefit 430 can include immediate access to a registered nurse 432. The access to the registered nurse can be by a voice or video call. The registered nurse can triage symptoms of the user and determine if emergency services (e.g., ambulance, emergency department, etc.) or urgent care services (e.g., after hours physicians) are needed. In another example, the emergency benefit 430 can immediate connect to an emergency service (e.g., 911, emergency department, etc.), The emergency benefit 430 can also present access to a website 434 to provide further information about emergency services and benefits.

Figure 5:
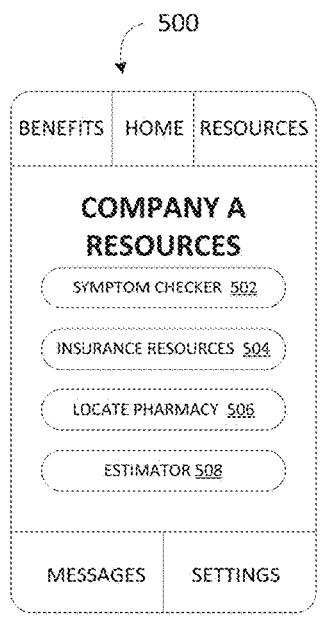

Referring now to FIG. 5, the client interface can present resources 500. For example, resources 500 can display available resources to the user (e.g., based on the user's healthcare profile, insurance coverage/benefits, company benefits, etc.). In some examples, unavailable resources can be a different color (e.g., grayed out) or be disabled (e.g., not selectable). Resources can include, but are not limited to, symptom checker 502, insurance resources 504, pharmacy locator 506, and/or healthcare estimator 508. The resources are selectable by input, at the client interface, from a user of client device 102. In some examples, input can be received from a touch screen/touch pads of client device 102. In other examples, the input can be through a mouse and/or keyboard. When an available resource is selected, the client interface can present data (received from healthcare server 106) corresponding to the selected resource as shown in FIGS. 6-10.

Figure 6:

Referring now to FIG. 6, symptom checker 600 can be presented on the client interface. Symptom checker 600 can receive input data 602 (e.g., from a user), submit the input data 604, and display diagnoses based on the input data. For example, if the user inputs symptoms including fever, fatigue, muscle aches, nausea, and diarrhea, symptom checker resource 600 can present that the user may suffer from the flu, along with a recommendation on medical services. In some examples, personal information from the healthcare profile of the user (or manually entered by the user) can be provided along with the one or more symptoms to provide more accurate results. Symptoms can be manually entered or selected from a list provided at the client interface. In another example, the personal information can be provided by a wearable electronic device, non-wearable personal use medical devices, or a user application. In another example the user input can be by Human API.

Figure 7A:
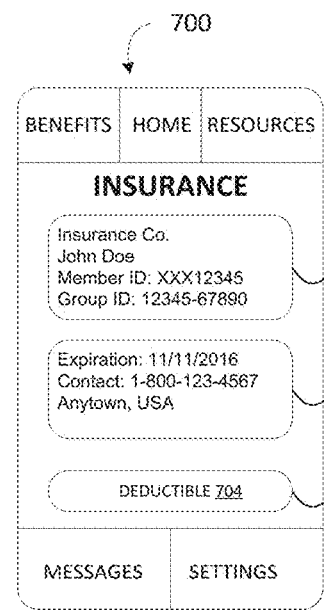
Figure 7B:
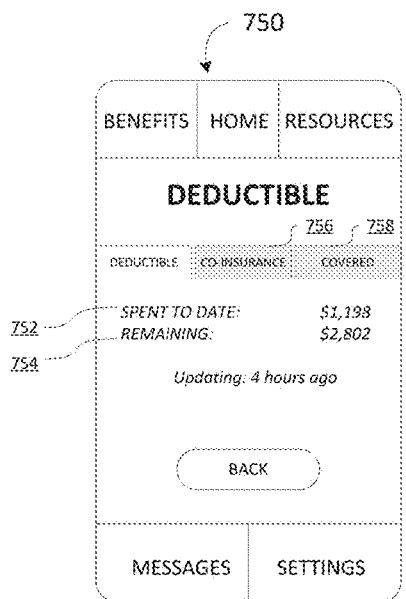

Referring now to FIG. 7A-7B, insurance resources 700 can be presented on the client interface. Insurance resources 700 can present current, historical, and/or insurance information/coverage/benefits of the user. The insurance information of the user can be based on the user's healthcare profile. The insurance information can be verified by insurance companies, and/or third-party services to determine insurance benefits/coverage. In some examples, the user's insurance card 702 can be presented. The insurance information/coverage/benefits can include, but are not limited to, the user's insurance card, deductibles, medical claims, flexible spending accounts, etc. The insurance information can be directly linked and verified with the benefits of FIG. 3-FIGS. 4A-D. The insurance information presented can be entered/updated by the user or a user's employer. In some examples, the user's insurance deductible 750 can be viewed. For examples, a user can select deductible 704 to view information on deductibles. In response to the user input, the client interface can present the deductible resource 750. The deductible resource 750 can be generated from the user's healthcare profile, the insurance company, and/or third-party services. In some examples, deductible information can include the out-of-pocket amount spent 752 and the remaining deductible 754. In other examples, deductible information can include past and/or pending transactions. In other examples, deductible resource 750 can display coinsurance information 756 and insurance covered medical services/procedures 758.

Figure 8:
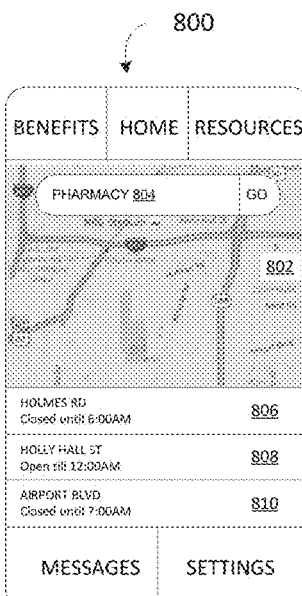

Referring now to FIG. 8, pharmacy locator resource 800 can be presented on the client interface. Pharmacy locator resource 800 can present a map interface 802 and search engine 804 for inputting and displaying pharmacies in a specified location. For example, a user can input a name of a pharmacy in search engine 804, and in response the client interface can display a map 802 and a list of pharmacies 806, 808 and 810 within the specified location (e.g., from the current location of client device 102, inputted location, etc.). In other examples, the user can input in search engine 804 a location (e.g., address, a zip code, a city, etc.). In other examples, the current location of client device 102 can be used to generate a list of pharmacies (e.g., determined by GPS, pinpointing a location based on distances related to other devices, etc.). The pharmacy list can be filtered by distance, store hours, store name, or any other attribute. In other examples, map interface 802 can provide directions for navigation to the location of the pharmacies from the pharmacy list.

Figure 9:
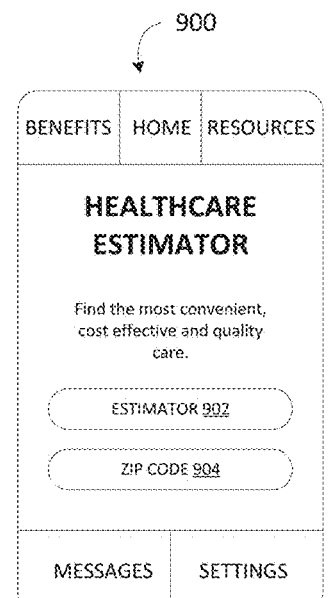

Referring now to FIG. 9, healthcare estimator resource 900 can be presented on the client interface. Healthcare estimator resource 900 can estimate the cost of a healthcare procedure. In some examples, the estimate can be based on location that the procedure will be performed. Healthcare estimator resource 900 can include an input 902 for the healthcare procedure (e.g., surgery, MRI, X-Ray, etc.) and an input 904 for location (e.g., zip code, city, state, etc.). In some examples, the location can be determined by the location of client device 102 (e.g., by GPS, pinpointing a location based on distances related to other devices, etc.). In response to a request of a healthcare estimate, client interface can display a healthcare pricing list including estimated prices for procedures, appointments, emergency visits, medicines, or tests (i.e., related to input 902 and 904). In some examples, the healthcare pricing list can be ordered based on attributes (e.g., selected by the user). Attributes can be, but are not limited to, price, distance, service, and/or reviews. For example, the user can input at the client interface of client device 102 a pricing request for an appointment for a checkup with a primary care physician for the flu within 5 miles of the user. A healthcare pricing list of primary care physicians that can treat the flu that are within 5 miles of the user can be generated and displayed on the client interface. When the user chooses a primary care physician, the physician profile (e.g., including contact details, an appointment calendar, etc.) can be presented to the user by the client interface.

Figure 10:
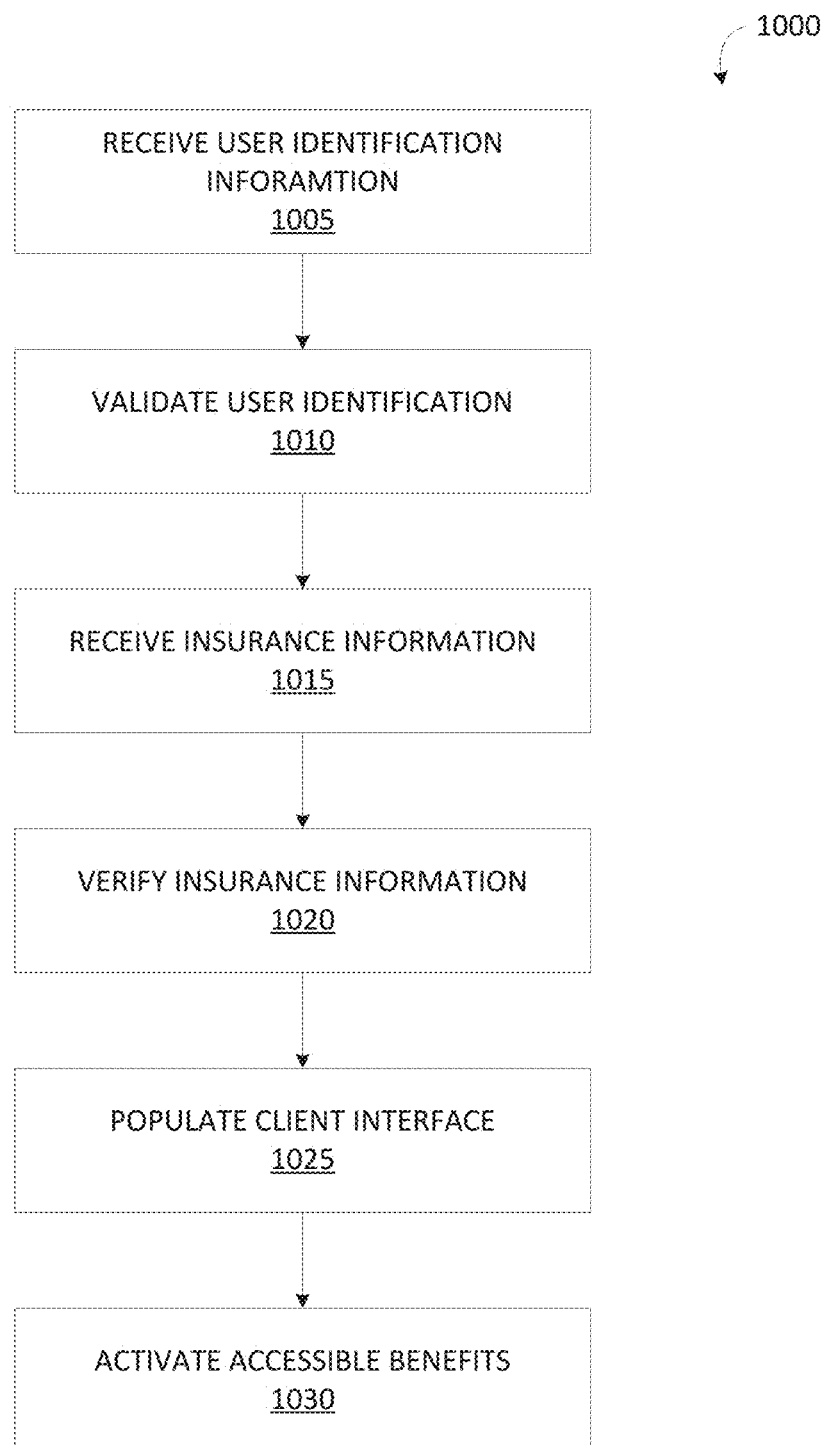
FIG. 10 is a flow chart of an example method of an integrated healthcare system.

The method shown in FIG. 10 is provided by way of example, as there are a variety of ways to carry out the method. Additionally, while the example method is illustrated with a particular order of blocks, those of ordinary skill in the art will appreciate that FIG. 10 and the blocks shown therein can be executed in any order that accomplishes the technical advantages of the present disclosure and can include fewer or more blocks than illustrated.

Each block shown in FIG. 10 represents one or more processes, methods or subroutines, carried out in the example method. The blocks shown in FIG. 10 can be implemented in a system such as system 100 shown in FIG. 1. The flow chart illustrated in FIG. 10 will be described in relation to and make reference to at least the elements of system 100 shown in FIG. 1 and the client interfaces shown in FIGS. 2-9.

Method 1000 can begin at block 1005. At block 1005 healthcare server 106 can receive user identification credentials. The user identification credentials can include the user's name, date of birth, social security number, company identifier, etc. Healthcare server 106 can in response to receiving the user identification credentials authenticate the user. In some examples, the healthcare server can receive initial user identification credentials (e.g., the first time a user attempts to use the healthcare services). During the initial authentication, a user can be prompted to establish a user account and profile, along with the verification of employment and insurance coverage. When healthcare server 106 has received user identification credentials, method 1000 can proceed to block 1010.

At block 1010, healthcare server 106 can validate the user. For example, during initial authentication, the user can be validated by a company list (i.e., to ensure the user is employed by the company). The validation can be performed at healthcare server 106 or by a third-party validation service (to which healthcare server 106 is communicatively coupled). In some examples, healthcare server 106 can receive user identification (e.g., name, date of birth, social security number, etc.) and a company identifier (e.g., name, unique identifier, etc.). Healthcare server 106 can retrieve a company list from database 108 based on the company identifier. The user identification can then be validated based on a comparison with the retrieved company list. When the user has been validated, method 1000 can proceed to block 1015.

At block 1015, healthcare server 106 can receive insurance information. For example, the user can provide insurance information at the client interface of client device 102 (e.g., manually entering insurance identification, scanning 3D barcode, uploading photograph of insurance card, etc.). In some examples, healthcare server 106 can receive insurance information from the company employing the user, a third-party server, the insurance company, etc. When healthcare server 106 has received insurance information, method 1000 can proceed to block 1020.

At block 1020, healthcare server 106 can verify insurance information to determine coverage/benefits. For example, healthcare server 106 can determine based on received insurance information that the user has insurance coverage/benefits, and the levels of insurance coverage/benefits. In some examples, healthcare server 106 can provide insurance information (i.e., received in block 1015) to the insurances company for verification. In other examples, a third-party verification service (e.g., affiliated with the insurance company) can verify insurance coverage/benefits. In response, the healthcare server 106 can receive verification of insurance information (e.g., available benefits, coverage levels, etc.). Healthcare server 106 can store the received verifications in database 108. Healthcare server 106 can also received an expiration date of the insurance coverage/benefits. Upon the expiration (or close to expiration) of the insurance coverage/benefit the user can be prompted to update the insurance information. When insurance information has been verified, method 1000 can proceed to block 1025.

At block 1025, the client interface can receive and populate insurance and benefits information. For example, the client interface of client device 102 can populate insurance information 700 and insurance card 702. The client interface can also populate deductible information 750. Client device 102 can store the received insurance and benefits information (i.e., from healthcare server 106) in the healthcare profile of the user (e.g., at a local memory or cache). When insurance information is received and populated, method 1000 can proceed to block 1030.

At block 1030, the client interface can activate accessible benefits to the user. For example, upon receiving benefits information at block 1025, the client interface of client device 102 can activate benefits available to the user. For example, if the benefits information enables access to PCP benefits, but not specialist benefits, then the PCP benefits 410 are activated and specialist benefits 420 are not activated. In other examples, PCP benefits 410 and specialist benefits 420 can be activated, but expedite appointment 404 and call specialist nurse 422 can be not activated. Any different combination of benefits can be activated. The activated benefits can be based on benefit information provided from the company and/or insurance information. When the benefits have been activated, method 1000 can end.

Figure 11:
FIG. 11 is a flow chart of an example method of generating a client interface.

The method shown in FIG. 11 is provided by way of example, as there are a variety of ways to carry out the method. Additionally, while the example method is illustrated with a particular order of blocks, those of ordinary skill in the art will appreciate that FIG. 11 and the blocks shown therein can be executed in any order that accomplishes the technical advantages of the present disclosure and can include fewer or more blocks than illustrated.

Each block shown in FIG. 11 represents one or more processes, methods or subroutines, carried out in the example method. The blocks shown in FIG. 11 can be implemented in a system such as system 100 shown in FIG. 1. The flow chart illustrated in FIG. 11 will be described in relation to and make reference to at least the elements of system 100 shown in FIG. 1 and the client interfaces shown in FIGS. 2-9.

The example method 1100 can begin at block 1105. At block 1105, a healthcare profile is identified. For example, a client device 102 can authenticate a user with a healthcare server 106 running a healthcare service (e.g., by a client interface). When successfully authenticated, the healthcare server 106 can transit information to the client interface to display a user's healthcare profile. The healthcare profile can include personal information related to the user or secondary users (e.g., user's family) and insurance information. If the authenticated user does not have a healthcare profile, the user can be prompted to create a healthcare profile. When a healthcare profile has been identified, the method 1100 can proceed to block 1110.

At block 1110, the client interface can display available benefits. The available benefits can be based on the insurance information and/or company provided benefits stored in the healthcare profile of the user of client device 102. The available benefits can also be determined from data received from an insurance company or a third-party service providing verification of insurance benefits. For example, after authentication, the client interface can display benefits screen 300. The client interface can receive an input for an available benefit (e.g., concierge benefit 302, primary care physicians benefit 304, specialists benefit 306, or emergency care benefit 308). When the available benefits have been displayed, method 1100 can proceed to block 1115.

At block 1115, one or more inputs are detected at client device 102 through the client interface. The input can be a selection of an available benefit (concierge benefit 302, primary care physicians benefit 304, specialists benefit 306, emergency care benefit 308, etc.). In some examples, the input can also be a request to generate a physician list for the available benefit (e.g., physician list 416). In other examples, the input can be to request communication with an emergency service (e.g., voice/video call with an emergency nurse 432). In other examples, the input can be to request a listing of specialists 426 or a telemedicine session with a specialist. In other examples, the input can be to initiate communication with a concierge 408. When the input has been received, method 1100 can proceed to block 1120.

At block 1120, a response to the input can be generated by healthcare server 106 and displayed at the client interface of client device 102. For example, when the input is a selection of an available benefit, the options under that available are generated and displayed (e.g., when PCP benefit is selected, PCP benefits 410 can be generated and displayed). In other examples, when the input is to find a physician (e.g., PCP, specialist, etc.) a physician list is generated and displayed on the client interface. The physician list can be based on the user's healthcare profile and input from the user (e.g., after find a physician 416 is selected at the primary care physician benefit 410, a PCP list is generated from the database 108 and displayed on the client interface of client device 102). The physician list can be filtered or adjusted based on attributes (e.g., specified by the user or automatically specified), such as, specialty, availability, telemedicine, conference capabilities, geographical location, etc. Through client interface of client device 102, an appointment can be scheduled or a session initiated (e.g., telemedicine, voice call, video call, chat, etc.). When a response has been generated, method 1100 can end.

Figure 12A:
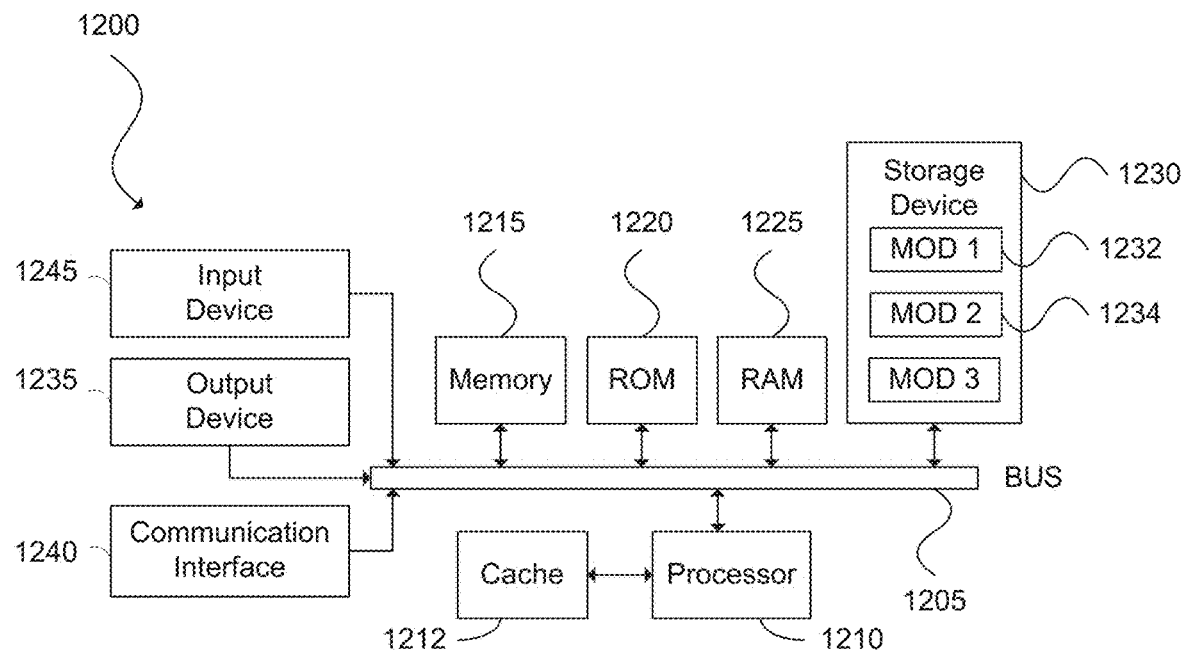
FIG. 12A shows an example system for implementing various embodiments of the present technology.
Figure 12B:
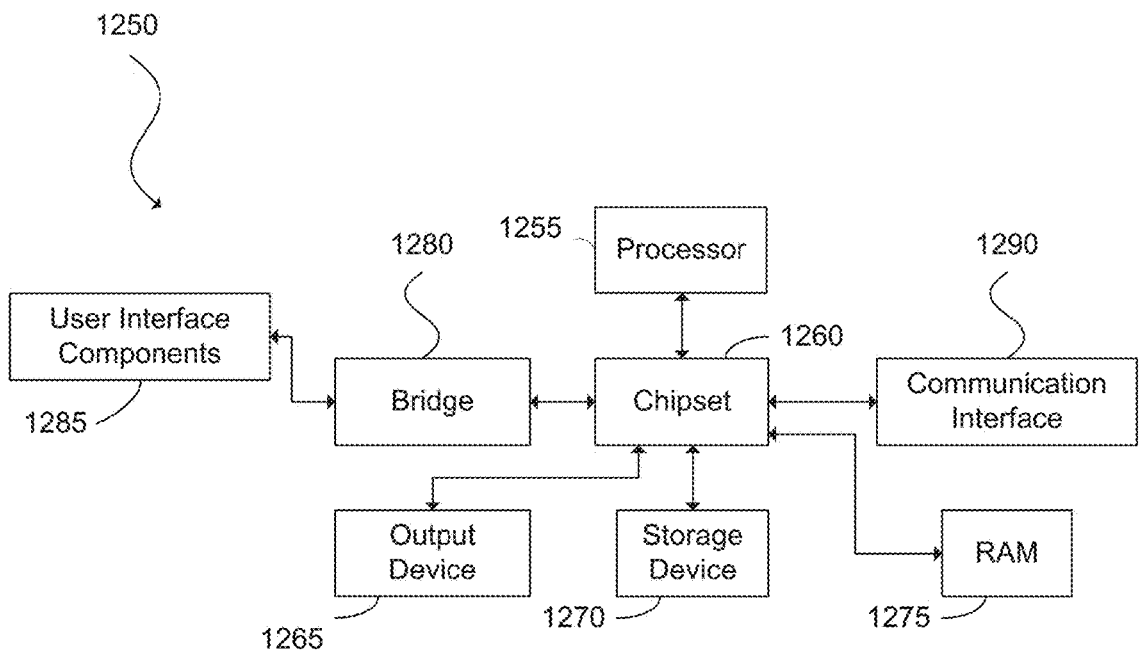
FIG. 12B shows an example system for implementing various embodiments of the present technology.

FIG. 12A and FIG. 12B show exemplary possible system examples. The more appropriate example will be apparent to those of ordinary skill in the art when practicing the present technology. Persons of ordinary skill in the art will also readily appreciate that other system examples are possible.

FIG. 12A illustrates a conventional system bus computing system architecture 1200 wherein the components of the system are in electrical communication with each other using a bus 1205. Exemplary system 1200 includes a processing unit (CPU or processor) 1210 and a system bus 1205 that couples various system components including the system memory 1215, such as read only memory (ROM) 1220 and random access memory (RAM) 1225, to the processor 1210. The system 1200 can include a cache of high-speed memory connected directly with, in close proximity to, or integrated as part of the processor 1210. The system 1200 can copy data from the memory 1215 and/or the storage device 1230 to the cache 1212 for quick access by the processor 1210. In this way, the cache can provide a performance boost that avoids processor 1210 delays while waiting for data. These and other modules can control or be configured to control the processor 1210 to perform various actions. Other system memory 1215 may be available for use as well. The memory 1215 can include multiple different types of memory with different performance characteristics. The processor 1210 can include any general purpose processor and a hardware module or software module, such as module 1 1232, module 2 1234, and module 3 1236 stored in storage device 1230, configured to control the processor 1210 as well as a special-purpose processor where software instructions are incorporated into the actual processor design. The processor 1210 may essentially be a completely self-contained computing system, containing multiple cores or processors, a bus, memory controller, cache, etc. A multi-core processor may be symmetric or asymmetric.

To enable user interaction with the computing device 1200, an input device 1245 can represent any number of input mechanisms, such as a microphone for speech, a touch-sensitive screen for gesture or graphical input, keyboard, mouse, motion input, speech and so forth. An output device 1235 can also be one or more of a number of output mechanisms known to those of skill in the art. In some instances, multimodal systems can enable a user to provide multiple types of input to communicate with the computing device 1200. The communications interface 1240 can generally govern and manage the user input and system output. There is no restriction on operating on any particular hardware arrangement and therefore the basic features here may easily be substituted for improved hardware or firmware arrangements as they are developed.

Storage device 1230 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1225, read only memory (ROM) 1220, and hybrids thereof.

The storage device 1230 can include software modules 1232, 1234, 1236 for controlling the processor 1210. Other hardware or software modules are contemplated. The storage device 1230 can be connected to the system bus 1205. In one aspect, a hardware module that performs a particular function can include the software component stored in a computer-readable medium in connection with the necessary hardware components, such as the processor 1210, bus 1205, display 1235, and so forth, to carry out the function.

FIG. 12B illustrates a computer system 1250 having a chipset architecture that can be used in executing the described method and generating and displaying a graphical user interface (GUI). Computer system 1250 is an example of computer hardware, software, and firmware that can be used to implement the disclosed technology. System 1250 can include a processor 1255, representative of any number of physically and/or logically distinct resources capable of executing software, firmware, and hardware configured to perform identified computations. Processor 1255 can communicate with a chipset 1260 that can control input to and output from processor 1255. In this example, chipset 1260 outputs information to output 1265, such as a display, and can read and write information to storage device 1270, which can include magnetic media, and solid state media, for example. Chipset 1260 can also read data from and write data to RAM 1275. A bridge 1280 for interfacing with a variety of user interface components 1285 can be provided for interfacing with chipset 1260. Such user interface components 1285 can include a keyboard, a microphone, touch detection and processing circuitry, a pointing device, such as a mouse, and so on. In general, inputs to system 1250 can come from any of a variety of sources, machine generated and/or human generated.

Chipset 1260 can also interface with one or more communication interfaces 1290 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1255 analyzing data stored in storage 1270 or 1275. Further, the machine can receive inputs from a user via user interface components 1285 and execute appropriate functions, such as browsing functions by interpreting these inputs using processor 1255.

It can be appreciated that exemplary systems 1200 and 1250 can have more than one processor 1210 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some examples the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Examples within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be utilized to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other examples of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

What is claimed is:

1. An integrated healthcare system comprising:
a healthcare server including:
a first processor; and
a non-transitory memory configured to store instructions for execution by the first processor, the instructions configured to cause the first processor to:
receive user identification data;
validate the user identification data includes at least a company identifier;
receive coverage information associated with the user identification data and the company identifier;
verify the coverage information; and
transmit, to one or more client devices, the validated user
identification data and verified coverage information; and
the one or more client devices, configured to be coupled to the healthcare server, including:
a second processor; and
a second non-transitory memory configured to store instructions for execution by the second processor, the instructions configured to cause the second processor to:
display, on a client interface of a client device, one or more available benefits based on the validated user identification data and the verified coverage information, the client interface comprising interactable icons corresponding to the one or more available benefits, the one or more benefits based on the verified coverage information;
receive, at the client interface of the client device, an input command through the interactable icons indicating selection of at least one of the one or more available benefits, the input command comprising a touch input from a touch screen display displaying the client interface and corresponding to a selection of a primary care service benefit;
generate a physician list that includes one or more available physicians, wherein the physician list is filtered based on one or more selected attributes, the one or more attributes selected at the client interface of the client device; and
initiate a first telemedicine session, the first telemedicine session comprising a video call putting the client device into communication with a selected physician from the filtered physician list, the physician selected at the client interface of the client device.

2. The integrated healthcare system of claim 1, wherein the client memory includes further instructions which when executed by the processor, cause the processor to:
transmit coverage information;
receive verification of the coverage information; and
populate the user interface with the coverage information.

3. The integrated healthcare system of claim 1, wherein the instructions are configured to cause the second processor to further initiate a second telemedicine session, the second telemedicine session comprising a video call putting the client device into communication with a registered nurse, wherein the registered nurse determines a specialist to put the client device into communication with.

4. The integrated healthcare system of claim 1, wherein the one or more available benefits comprise one or more of a concierge, a primary care physician, a specialist, or an emergency care service.

5. The integrated healthcare system of claim 1, wherein the first telemedicine session is a communication with a concierge.

6. The integrated healthcare system of claim 5, wherein the concierge is a person.

7. The integrated health system of claim 1, wherein the initiation of the first telemedicine session includes retrieving one or more records associated with the user identification data.

8. The integrated healthcare system of claim 1, wherein the initiation of the first telemedicine session includes scheduling an appointment.

9. The integrated healthcare system of claim 1, wherein the user interface displays a coverage card based on the verified coverage information.

10. A client computer configured to receive data from a healthcare server, the client computer comprising:
   a processor;
   a display coupled to the processor and configured to display a client interface;
   a non-transitory memory configured to store instructions for execution by the processor, the instructions configured to cause the processor to:
     receive, at the client interface, user identification data;
     transmit, to the healthcare server, the user identification data;
     receive, from the healthcare server, validation that the user identification data includes at least a company identifier;
     receive, from the healthcare server, coverage information associated with the user identification data and the company identifier;
     verify the coverage information;
     display, on the client interface, one or more available benefits based on the validation of the user identification data and the verified coverage information, the client interface comprising interactable icons corresponding to the one or more available benefits, the one or more benefits based on the verified coverage information;
     receive, at the client interface, an input command through the interactable icons indicating selection of at least one of the one or more available benefits, the input command comprising a touch input from a touch screen display displaying the client interface and corresponding to a selection of a primary care service benefit;
     generate a physician list that includes one or more available physicians, wherein the physician list is filtered based on one or more selected attributes, the one or more attributes selected at the client interface; and
     initiate a first telemedicine session, the first telemedicine session comprising a video call putting the client device into communication with a selected physician from the filtered physician list, the physician selected at the client interface.

11. The client computer of claim 10, wherein the non-transitory memory includes further instructions which when executed by the processor, cause the processor to:
   transmit coverage information; and
   populate the user interface with the coverage information.

12. The client computer of claim 10, wherein the instructions are configured to cause the processor to further initiate a second telemedicine session, the second telemedicine session comprising a video call putting the client device into communication with a registered nurse, wherein the registered nurse determines a specialist to put the client device into communication with.

13. The client computer of claim 10, wherein the one or more available benefits comprise one or more of a concierge, a primary care physician, a specialist, or an emergency care service.

14. The client computer of claim 10, wherein the first telemedicine session is conducted with a concierge.

15. The client computer of claim 14, wherein the concierge is a human.

16. The client computer of claim 10, wherein the initiation of the first telemedicine session includes retrieving one or more records associated with the user identification data.

17. The client computer of claim 10, wherein the initiation of the first telemedicine session includes scheduling an appointment.

18. The client computer of claim 10, wherein the user interface displays a coverage card based on the verified coverage information.

19. A healthcare server configured to receive data from a client computer, the healthcare server comprising:
   a processor; and
   a non-transitory memory configured to store instructions for execution by the processor, the instructions configured to cause the processor to:
     receive user identification data;
     validate the user identification data includes at least a company identifier;
     receive coverage information associated with the user identification data and the company identifier;
     verify the coverage information; and
     transmit, to one or more client devices, the validated user identification data and the verified coverage information, the validated user identification data and the verified coverage information used to trigger a client interface of a client device to:
       display one or more available benefits based on the validated user identification data and the verified coverage information, the client interface comprising interactable icons corresponding to the one or more available benefits, the one or more benefits based on the verified coverage information;
       receive an input command through the interactable icons indicating selection of at least one of the one or more available benefits, the input command comprising a touch input from a touch screen display displaying the client interface and corresponding to a selection of a primary care service benefit;
       generate a physician list that includes one or more available physicians, wherein the physician list is filtered based on one or more selected attributes, the one or more attributes selected at the client interface of the client device; and
       initiate a first telemedicine session, the first telemedicine session comprising a video call putting the client device into communication with a selected physician from the filtered physician list, the physician selected at the client interface of the client device.

20. The healthcare server of claim 19, wherein the non-transitory memory includes further instructions which when executed by the processor, cause the processor to:
   determine available benefits, based on the verified coverage information; and
   transmit, to the client computer, the available benefits;

wherein the triggered first telemedicine session is based on a selection of one of the available benefits, the selection comprising a touch input from a touch screen display displaying the user interface, the one of the available benefits comprising an emergency care service benefit.

* * * * *